US00PP29686P3

(12) United States Plant Patent
Jacobs

(10) Patent No.: US PP29,686 P3
(45) Date of Patent: Sep. 18, 2018

(54) ***ALSTROEMERIA* PLANT NAMED 'ZAPRILIARANGE'**

(50) Latin Name: *Alstroemeria hybrida*
Varietal Denomination: Zapriliarange

(71) Applicant: Henricus Cornelius Maria Jacobs, Bleiswijk (NL)

(72) Inventor: Henricus Cornelius Maria Jacobs, Bleiswijk (NL)

(73) Assignee: Van Zanten Plants B.V., Rijsenhout (NL)

( * ) Notice: Subject to any disclaimer, the term of this patent is extended or adjusted under 35 U.S.C. 154(b) by 21 days.

(21) Appl. No.: 15/530,423

(22) Filed: Jan. 12, 2017

(65) Prior Publication Data

US 2018/0199488 P1 Jul. 12, 2018

(51) Int. Cl.
*A01H 5/02* (2018.01)

(52) U.S. Cl.
USPC ..... Plt./309

(58) Field of Classification Search
USPC ..... Plt./309
See application file for complete search history.

*Primary Examiner* — Keith O Robinson
(74) *Attorney, Agent, or Firm* — C. A. Whealy

(57) ABSTRACT

A new and distinct cultivar of *Alstroemeria* plant named 'Zapriliarange', characterized by its compact, upright to outwardly spreading and uniformly mounded plant habit; vigorous growth habit; rapid growth rate; numerous orange-colored flowers with greyed purple-colored stripes on the inner perianth segments; and excellent container and garden performance.

2 Drawing Sheets

Botanical designation: *Alstroemeria hybrida.*
Cultivar denomination: 'ZAPRILIARANGE'.

BACKGROUND OF THE INVENTION

The present invention relates to a new and distinct cultivar of *Alstroemeria* plant, botanically known as *Alstroemeria hybrida*, commercially used as a potted and garden-type *Alstroemeria* plant and hereinafter referred to by the name 'Zapriliarange'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant is a naturally-occurring whole plant mutation of *Alstroemeria hybrida* 'Zaprielia', disclosed in U.S. Plant Pat. No. 22,338. The new *Alstroemeria* plant was discovered and selected by the Inventor as a single flowering plant from within a population of plants of 'Zaprielia' in a controlled greenhouse environment in Rijsenhout, The Netherlands in March, 2011.

Asexual reproduction of the new *Alstroemeria* plant by rhizome divisions in a controlled greenhouse environment in Rijsenhout, The Netherlands since June, 2011 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Zapriliarange'. These characteristics in combination distinguish 'Zapriliarange' as a new and distinct potted *Alstroemeria* plant:

1. Compact, upright to outwardly spreading and uniformly mounded plant habit.
2. Vigorous growth habit and rapid growth rate.
3. Numerous orange-colored flowers with greyed purple-colored stripes on the inner perianth segments.
4. Excellent container and garden performance.

Plants of the new *Alstroemeria* differ primarily from plants of the mutation parent, 'Zaprielia' in flower color as plants of 'Zaprielia' have dark pink-colored flowers. In addition, plants of the new *Alstroemeria* are taller than plants of 'Zaprielia'.

Plants of the new *Alstroemeria* can be compared to plants of *Alstroemeria hybrida* 'Zapriliali', disclosed in U.S. Plant patent application Ser. No. 15/530,422. In side-by-side comparisons, plants of the new *Alstroemeria* differ primarily from plants of 'Zapriliali' in flower color as plants of 'Zapriliali' have light pink-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Zapriliarange' grown in a container.

The photograph on the second sheet is a close-up view of a typical flowering plant of 'Zapriliarange'.

DETAILED BOTANICAL DESCRIPTION

The aforementioned photographs and following observations and measurements describe plants of the new *Alstroemeria* grown during the late winter and early spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperature averaged 14° C. and minimum light levels were 5,000 lux. Plants were three months old when the photographs and the description were taken. In the following description, color references are made to The Royal Horticultural Society Colour Chart, 2007 Edition, except where general terms of ordinary dictionary significance are used.

Botanical classification: *Alstroemeria hybrida* 'Zapriliarange'.

Parentage: Naturally-occurring whole plant mutation of *Alstroemeria hybrida* 'Zaprielia', disclosed in U.S. Plant Pat. No. 22,338.

Propagation:

*Type*.—In vitro rhizogenesis.

*Time to produce a rooted young plant, summer*.—About 40 days.

*Time to produce a rooted young plant, winter*.—About 60 days.

*Root description*.—Fibrous, fleshy, thick; close to 155D in color.

*Rooting habit*.—Freely branching; medium density.

*Rhizomes*.—Shape: Elongate; rounded. Length: About 10 cm to 30 cm. Diameter: About 3 mm to 10 mm. Texture: Smooth. Color: Close to 155D.

Overall plant description:

*Plant and growth habit*.—Compact, upright to outwardly spreading and uniformly mounding plant habit; freely branching habit with numerous lateral branches, dense and bushy appearance; vigorous growth habit; rapid growth rate.

*Plant height*.—About 26 cm to 28 cm.

*Plant diameter* (*spread*).—About 40 cm to 45 cm.

Lateral branch description:

*Aspect*.—Mostly upright.

*Length*.—About 8.1 cm to 10 cm.

*Diameter*.—About 2 mm to 3 mm.

*Internode length*.—About 3 mm to 10 mm.

*Strength*.—Strong.

*Texture*.—Smooth, glabrous.

*Color*.—Close to 145C.

Leaf description:

*Appearance*.—Simple, asymmetrical; sessile.

*Length*.—About 7.5 cm to 10 cm.

*Width*.—About 1.7 cm to 2.6 cm.

*Shape*.—Lanceolate.

*Apex*.—Acute.

*Base*.—Cuneate.

*Margin*.—Entire.

*Texture, upper and lower surfaces*.—Smooth, glabrous; matte.

*Venation pattern*.—Parallel.

*Color*.—Developing and fully expanded leaves, upper surface: Close to 147A; venation, close to 141D. Developing and fully expanded leaves, lower surface: Close to 147B; venation, close to 137D.

Flower description:

*Flower type and habit*.—Single cup-shaped flowers arranged in compound umbels; flowers face mostly outwardly; perianth segments separate; freely flowering habit with about five flowers developing per inflorescence.

*Natural flowering season*.—Flowering continuous during the spring in The Netherlands; early flowering habit, plants begin flowering about 70 to 80 days after planting.

*Fragrance*.—None detected.

*Flower longevity on the plant*.—About four weeks; flowers not persistent.

*Flower buds*.—Length: About 4.3 cm to 4.5 cm. Diameter: About 1.3 cm to 1.5 cm. Shape: Roughly ovoid. Color: Close to 179B to 179C.

*Umbel height*.—About 7 cm to 9 cm.

*Umbel diameter*.—About 11 cm to 12 cm.

*Flower diameter*.—About 5.5 cm.

*Flower depth*.—About 6.5 cm.

*Perianth*.—Arrangement: Six arranged in two whorls, each whorl with two lateral and one median segments. Inner perianth, lateral segments: Length: About 5.4 cm to 6.2 cm. Width: About 1.8 cm to 2.1 cm. Shape: Oblanceolate. Apex: Wishbone-shaped. Base: Attenuate. Margin: Entire. Texture, upper and lower surfaces: Smooth, glabrous. Color, when opening and fully opened, upper surface: Close to 41C to 41D; center, close to 13D; stripes, close to 184B; color does not change with development. Color, when opening and fully opened, lower surface: Close to 41C to 41D; center, close to 13D; stripes, close to 184D; color does not change with development. Inner perianth, median segment: Length: About 5 cm to 5.5 cm. Width: About 1.9 cm to 2.1 cm. Shape: Oblanceolate. Apex: Wishbone-shaped. Base: Attenuate. Margin: Entire. Texture, upper and lower surfaces: Smooth, glabrous. Color, when opening and fully opened, upper surface: Close to 41C to 41D; stripes, close to 184B; color does not change with development. Color, when opening and fully opened, lower surface: Close to 41C to 41D; stripes, close to 184D; color does not change with development. Outer perianth, lateral segments: Length: About 5.4 cm to 5.8 cm. Width: About 3 cm to 3.6 cm. Shape: Obovate. Apex: Emarginate with an embedded point. Base: Attenuate. Margin: Shallowly serrate. Texture, upper and lower surfaces: Smooth, glabrous. Color, when opening and fully opened, upper surface: Close to 41C to 41D; apex, close to 143A; color does not change with development. Color, when opening and fully opened, lower surface: Close to 41C to 41D; venation, close to 143A; color does not change with development. Outer perianth, median segment: Length: About 5.2 cm to 5.7 cm. Width: About 3 cm to 3.5 cm. Shape: Obovate. Apex: Emarginate with an embedded point. Base: Attenuate. Margin: Shallowly serrate. Texture, upper and lower surfaces: Smooth, glabrous. Color, when opening and fully opened, upper surface: Close to 41C to 41D; apex, close to 143A; color does not change with development. Color, when opening and fully opened, lower surface: Close to 41C to 41D; venation, close to 143A; color does not change with development.

*Pedicels*.—Length: About 0.2 cm to 1.5 cm. Diameter: About 2 mm to 3 mm. Strength: Strong. Angle: About 20° to 30° from vertical. Texture: Smooth, glabrous. Color: Close to 138B.

*Reproductive organs*.—Stamens: Quantity per flower: Typically six. Anther shape: Elliptic. Anther length: About 5 mm to 6 mm. Anther color: Close to 185C. Pollen amount: Abundant. Pollen color: Close to 199A. Pistils: Quantity per flower: One. Style length: About 3.4 cm to 3.7 cm. Style color: Close to 179B. Stigma shape: Three-parted. Stigma color: Close to 179B. Ovary color: Close to 143C.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain and temperatures from about −5° C. to about 40° C.

It is claimed:

1. A new and distinct *Alstroemeria* plant named 'Zaprili-arange' as illustrated and described.

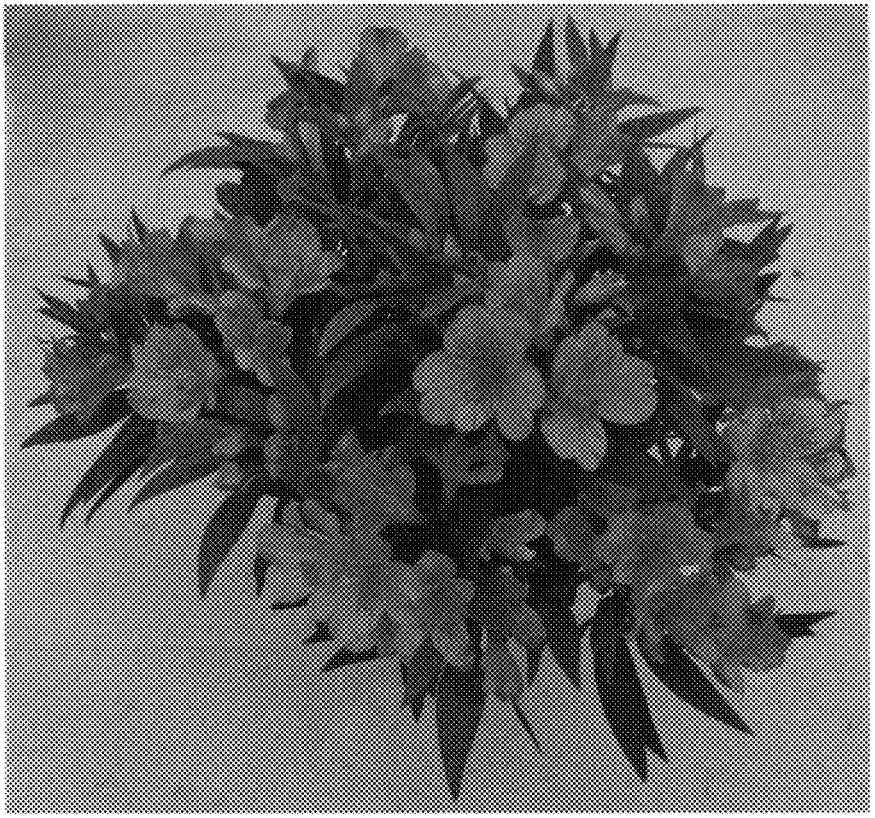

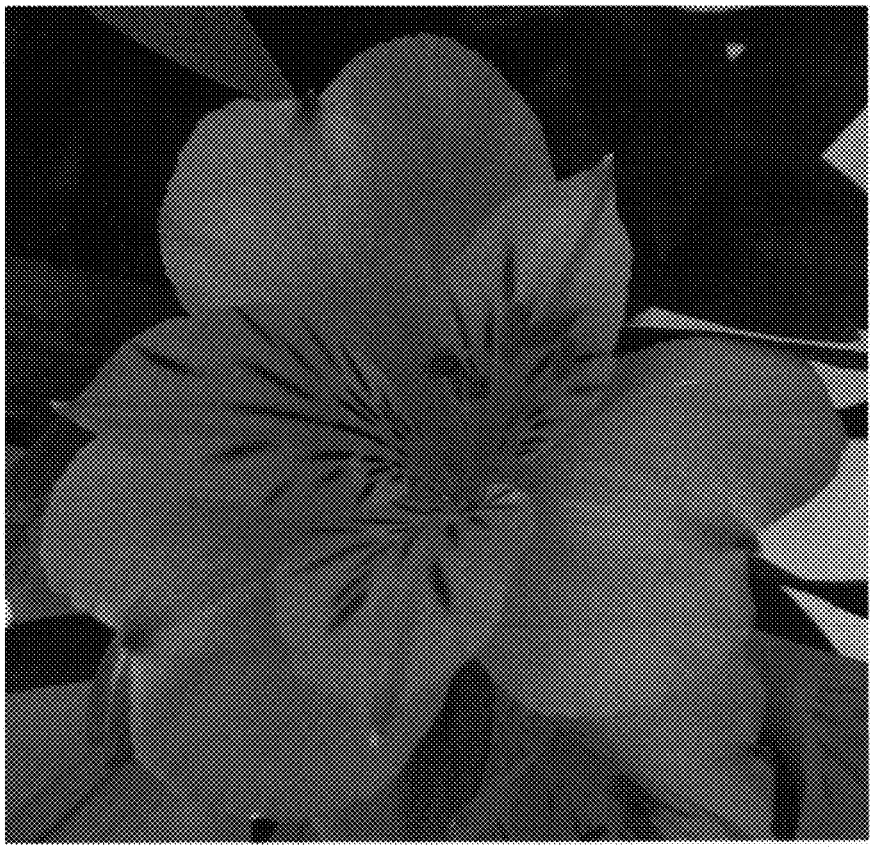

* * * * *